(12) United States Patent
Self

(10) Patent No.: US 8,062,855 B2
(45) Date of Patent: Nov. 22, 2011

(54) ASSAY METHODS AND MATERIALS

(75) Inventor: Colin Henry Self, Ponteland (GB)

(73) Assignee: Selective Antibodies Limited (GB)

( * ) Notice: Subject to any disclaimer, the term of this patent is extended or adjusted under 35 U.S.C. 154(b) by 749 days.

(21) Appl. No.: 10/570,393

(22) PCT Filed: Aug. 31, 2004

(86) PCT No.: PCT/GB2004/003718
§ 371 (c)(1),
(2), (4) Date: Nov. 30, 2006

(87) PCT Pub. No.: WO2005/022150
PCT Pub. Date: Mar. 10, 2005

(65) Prior Publication Data
US 2007/0178543 A1 Aug. 2, 2007

(30) Foreign Application Priority Data

Sep. 1, 2003 (GB) .................................. 0320459.1

(51) Int. Cl.
*G01N 31/00* (2006.01)
*G01N 33/53* (2006.01)

(52) U.S. Cl. ......... 435/7.21; 435/7.1; 436/501; 436/518

(58) Field of Classification Search ........................ None
See application file for complete search history.

(56) References Cited

U.S. PATENT DOCUMENTS

| 4,434,236 A | | 2/1984 | Freytag |
| 5,037,764 A | | 8/1991 | Wilk et al. |
| 5,641,690 A | * | 6/1997 | Self ............................... 436/548 |
| 6,074,644 A | * | 6/2000 | Pastan et al. ............... 424/178.1 |

| 2001/0024795 A1 | 9/2001 | Khaw et al. |
| 2002/0031781 A1 | 3/2002 | Khaw et al. |
| 2003/0078385 A1 | 4/2003 | Arathoon et al. |

FOREIGN PATENT DOCUMENTS

WO  WO 99/61055  * 12/1999

OTHER PUBLICATIONS

Kane et al. (Analytical Biochemistry, vol. 278, 2000, pp. 29-38).*
Koo et al. (Applied and Environmental Microbiology, Jul. 1998, pp. 2497-2502).*
Wong et al. (Journal of Immunology, 1995, vol. 154, pp. 3351-3358).*
Varshavsky (Proc. Natl. Acad. Sci. USA vol. 95, pp. 2094-2099, Mar. 1998).*
Briesewitz et al. (Proc. Natl. Acad. Sci, USA, vol. 96, pp. 1953-1958, Mar. 1999).*
Cao et al., "Bispecific Antibodies as Novel Bioconjugates", American Chemical Society, vol. 9, No. 6, Oct. 20, 1998, pp. 635-644.

* cited by examiner

*Primary Examiner* — Lisa Cook
(74) *Attorney, Agent, or Firm* — Arnold & Porter LLP; Ginger R. Dreger

(57) ABSTRACT

The invention relates to assays in which complexes between an analyte and a binding agent specific for the analyte are detected by a reporter molecule, which is capable of binding to the binding agent when the binding agent is complexed with analyte but not when the binding agent is complexed with an analyte analogue. The invention provides a method of modifying such a binding agent in order to create a tailored site where the reporter molecule may bind to the binding agent. This provides control over the location and nature of the reporter binding site. Antibodies, including bispecific antibodies, are preferred binding agents. The invention also provides novel methods for labelling antibodies close to their antigen binding site using bi- and tri-functional reagents. Modified binding agents produced by the methods described are also provided.

11 Claims, No Drawings

ASSAY METHODS AND MATERIALS

FIELD OF THE INVENTION

The present invention relates to biological assays for analytes, and in particular to assays in which complexes between an analyte and a binding agent are detected by a reporter molecule, which is capable of forming a complex with the binding agent when the binding agent is complexed with analyte but not when the binding agent is complexed with an analyte analogue.

BACKGROUND TO THE INVENTION

Immunodiagnostic methods have proved to be of great use both within and outside of clinical areas. Food testing, environmental testing and forensic applications are but some of the applications. The robustness, precision and convenience of the methods have led to applications ranging from kits for home use to sophisticated laboratory auto-analysers. In particular, the development of immunometric technologies for large molecular weight analytes has been outstandingly successful. A particular advantage of such technologies is that they produce an increasing signal with increasing concentration of analyte.

Classical competitive assay formats are very widely employed but have a fundamental difficulty in that they rely on setting up competition for a binding site between an analyte and an analyte analogue and thereafter measuring how much analyte analogue has been bound to the binding site. Thus they do not directly measure how much analyte has been bound. Such a method is described in Chapter 1 of ELISA and Other Solid Phase Immunoassays, Ed DM Kemeny & S J Challacombe, pub. Wiley, 1988. Other indirect assays which measure the number of binding sites not occupied by analyte are described in WO 95/04931 and WO 92/19973.

U.S. Pat. No. 5,641,690 discloses a method for determining an analyte using a specific binding agent. The analyte is mixed with an analyte analogue and contacted with the binding agent. Complexes between analyte and binding agent are detected by an antibody, which is typically specific for a site on the binding agent. The analyte analogue, however, is designed such that it prevents binding between antibody and binding agent when it is bound to the binding agent. This assay provides a way for directly measuring the number of binding sites occupied by analyte, thus enabling more sensitive and precise assays than those which rely on indirect detection of analyte binding. However these assays rely on being able to generate an antibody which binds sufficiently close to the analyte binding site for its interaction with the binding partner to be blocked by the chosen analyte analogue. This can be both time-consuming and costly.

SUMMARY OF THE INVENTION

Broadly, the present invention relates to assays similar to those described in U.S. Pat. No. 5,641,690 as described above in which complexes between analyte and binding agent are detected by a reporter molecule, which is capable of binding to the binding agent when the binding agent is complexed with analyte but not when the binding agent is complexed with an analyte analogue. Thus the binding agent has an analyte binding site which is capable of binding to either the analyte or the analyte analogue, but not to both at the same time.

In its broadest form, the invention provides a method of modifying a binding agent having an analyte binding site capable of binding either said analyte or an analyte analogue, said modification comprising creating a reporter site adapted to interact in a detectable manner with a reporter molecule when the modified binding agent is bound to analyte, but not when the modified binding agent is bound to analyte analogue. Modified binding agents produced by these methods are also provided.

The present invention provides a method of determining an analyte in a sample, comprising the steps of
(a) modifying a binding agent having an analyte binding site capable of binding either said analyte or an analyte analogue, said modification comprising creating a reporter site adapted to interact in a detectable manner with a reporter molecule when the modified binding agent is bound to analyte, but not when the modified binding agent is bound to analyte analogue; and
(b) contacting the sample with
(i) said analyte analogue;
(ii) said modified binding agent; and
(iii) said reporter molecule;
and optionally
(c) determining the amount of reporter molecule interacting with the modified binding agent.

This enables the binding agent to be tailored to the particular assay by providing control over the location and nature of the reporter site. This may, inter alia, allow a single reporter molecule to be used in assays involving different binding agents, as the various binding agents can all be engineered to contain the same reporter site.

This may also allow standardisation of analyte analogues for such assays. The location and nature of the reporter site can be chosen such that binding of an analyte analogue of a particular shape and/or size to the modified binding agent will interfere with interaction of the reporter molecule with the reporter site. This may allow analyte analogues to be designed around a common structural framework or molecular skeleton.

The binding agent may be any suitable molecule capable of binding to the analyte. Preferably the binding agent and analyte form a specific binding pair, as described in more detail below. In preferred embodiments the binding agent is an antibody or an enzyme.

In preferred embodiments, the reporter molecule is capable of binding to the reporter site. Binding between the reporter site and reporter molecule may then be detected by any suitable method. Preferably the reporter site and reporter molecule also form a specific binding pair.

Thus the modified binding agent may be capable of binding simultaneously to the analyte and the reporter molecule, but not to the reporter molecule and the analyte analogue. That is to say, when bound to the modified binding agent, the analyte analogue interferes with binding between the reporter molecule and the reporter site.

The analyte analogue may prevent binding between said reporter molecule and said binding agent by steric hindrance, electrostatic repulsion, or any other suitable mechanism.

The reporter site may be created by chemical modification of the binding agent, or by modification of nucleic acid encoding the binding agent. The reporter site may comprise a moiety having a detectable property which is modified by proximity to the reporter molecule, or vice versa. For example, the reporter site and reporter molecule may each comprise a fluorescent label whose emission spectra are altered when the two labels are in close proximity to one another.

Alternatively the reporter site may comprise a label capable of being bound by a specific reporter molecule, for example the reporter site may comprise a biotin moiety, capable of binding/being bound by avidin or streptavidin (or an anti-biotin antibody), or may be a peptide sequence having a known binding partner. In preferred embodiments the reporter site is a known epitope for an antibody, such as a monoclonal antibody.

Certain methods of chemical modification of the present invention make use of reagents capable of carrying two or three functionalities separated by a selectively cleavable group. This may be considered a method of introducing a label into a binding agent, the label being detectable with a suitable reporter molecule. Thus the label may constitute a reporter site as described above. However these methods may also be applicable in other contexts.

Thus the invention further provides a method of labelling a binding agent having an analyte binding site, comprising the steps of:

forming a complex between said binding agent and a labelling reagent, the labelling, reagent comprising a targeting moiety and a reactive group, wherein said complex is formed by binding of said targeting moiety to said binding site;

causing the reactive group to react with the binding agent; and causing the targeting moiety to dissociate from the binding agent.

The targeting moiety may comprise the analyte or a fragment or mimetic thereof capable of binding to the binding site.

The reaction between the binding agent and the reactive group of the labelling reagent may be initiated by irradiation, change in pH or temperature, addition of oxidising or reducing agents, etc. Preferably the reactive group is a photoactivatable moiety.

Following dissociation of the targeting moiety from the binding site, the targeting moiety may be chemically derivatised so that it can no longer interact with the binding site. The thus derivatised targeting moiety may serve as a reporter site when the labelled binding agent is used in an assay for the analyte as described herein.

Alternatively the labelling reagent may comprise a selectively cleavable group located between the targeting moiety and the reactive group. The method may further comprise the step of cleaving said selectively cleavable group. Cleavage may take place before or after the targeting moiety is dissociated from the analyte binding site.

The selectively cleavable group may be cleavable by irradiation, change in pH or temperature, addition of oxidising or reducing agents, etc. Preferably the selectively cleavable group is cleaved under conditions different to those required for causing the reactive group to react with the binding agent.

In preferred embodiments the selectively cleavable group is cleavable by reduction or irradiation. In particularly preferred embodiments, especially where the reactive group is a photoactivatable moiety, the selectively cleavable group is a disulphide bond.

The labelling reagent may further comprise a label moiety. Alternatively, a label moiety may be coupled to the labelling reagent after the labelling reagent has been coupled to the binding agent. The labelling moiety may be coupled to the labelling reagent via a group generated by cleavage of said selectively cleavable group, or the labelling reagent may possess a further reactive group, distinct from the selectively cleavable group, to facilitate such coupling of a label moiety.

The labelling reagent may comprise trifunctional reagents such as Sulfo-SBED (Geselowitz & Neumann (1995) Bioconjugate Chem, 6, 502-506).

The binding agent may be e.g. an antibody or an enzyme. Where the binding agent is an antibody, the targeting moiety of the labelling reagent may comprise the cognate epitope of said antibody.

Where the binding agent is an enzyme, the targeting moiety of the labelling reagent may comprise a substrate or modulator of said enzyme. Particularly where the analyte is a substrate for the enzyme, the enzyme may be inactivated, so that the analyte can bind to the active site without being chemically modified by the enzyme.

Also provided is a method of preparing a kit for use in determining an analyte in a sample, comprising (a) modifying a binding agent having an analyte binding site capable of binding either said analyte or an analyte analogue, said modification comprising creating a reporter site adapted to interact in a detectable manner with a reporter molecule when the modified binding agent is bound to analyte, but not when the modified binding agent is bound to analyte analogue; and (b) packaging together (i) said modified binding agent;

(ii) said reporter molecule; and (iii) said analyte analogue.

The binding agent may be modified by any of the methods described herein.

The kit may further comprise the analyte itself (e.g. for the construction of a standard curve for performing the assay), and/or a set of instructions for performing an apposition-type assay.

Modification of a binding agent as described herein may involve the formation of a bispecific antibody, having a first antigen binding site specific for an analyte, and a second antigen binding site specific for the reporter molecule; the second antigen binding site may be considered the reporter site of the binding agent described above.

In certain embodiments, therefore, there is provided a method of determining an analyte in a sample, comprising contacting the sample with (i) an antibody having a first antigen binding site capable of binding either said analyte or an analyte analogue, and a second antigen binding site capable of binding a reporter molecule;

(ii) said analyte analogue; and (iii) said reporter molecule;

wherein said second antigen binding site can bind the reporter molecule when the first antigen binding site is bound to analyte, but not when the first antigen binding site is bound to analyte analogue, and optionally determining the amount of reporter molecule bound to the second antigen binding site.

There is further provided a kit for determining an analyte in a sample, comprising (i) an analogue of said analyte;

(ii) a reporter molecule; and (iii) an antibody having a first antigen binding site capable of binding either said analyte or said analyte analogue and a second antigen binding site capable of binding said reporter molecule;

wherein said second antigen binding site is capable of binding the reporter molecule when the first antigen binding site is bound to analyte, but not when the first antigen binding site is bound to analyte analogue.

The kit may further comprise the analyte itself (e.g. for the construction of a standard curve for performing the assay), and/or a set of instructions for performing an apposition-type assay.

Any of the assays described herein may be performed in the solid phase. Thus the kits described above may provide a solid phase assay, e.g. a lateral flow-type assay for determining the presence of the analyte. The kit may be used for detecting the presence of the analyte in a biological fluid, e.g. a bodily fluid such as urine, blood, saliva, semen, tears or other secretions.

DETAILED DESCRIPTION OF THE INVENTION

The invention provides modified binding agents and their use in assays for desired analytes which rely on the ability of a reporter molecule to interact in a detectable manner with a complex between a binding agent and an analyte (e.g. by binding to that complex) but not a complex between a reporter molecule and an analyte analogue. Typically, the analyte analogue prevents binding of the reporter molecule to the analogue/binding agent complex, e.g. via steric hindrance or electrostatic repulsion, although other possible mechanisms will be apparent to the skilled person. The use of specifically modified binding agents provides a number of advantages as described above, such as standardisation of assays.

The binding agent may be modified either chemically or by genetic modification to create a reporter site which interacts with the reporter molecule. In preferred embodiments the reporter molecule is capable of binding to the reporter site.

Thus the assay relies on two principal molecular interactions; firstly, that between the binding site of the binding agent and the analyte or analyte analogue, and secondly the interaction between the reporter site of the binding agent and the reporter molecule (which interaction is prevented by binding of analyte analogue to the binding agent).

Preferably the interaction between binding site and analyte/analogue is a specific interaction. By "specific" is meant that the particular binding sites of the binding agent will not show any significant binding to molecules in the assay other than analyte or analogue. The affinity of the binding site for analyte or analogue is preferably at least 10 fold greater than for other molecules in the assay, preferably greater than 20 fold, preferably greater than 50 fold, and more preferably greater than 100 fold. Typically the affinity of the binding site for other molecules will be of the order of 1000 times worse than for analyte or analogue.

Preferably the binding agent has the same or substantially the same affinity for the analogue as for the analyte. The analyte analogue will typically comprise the same part of the analyte molecule as that recognised by the binding agent (see below), or a fragment or mimetic thereof. The analogue may comprise other moieties capable of binding to the analyte binding site, such as an antibody directed against the binding site. For example, where the binding agent is an antibody directed against the analyte, the analyte analogue may be an anti-idiotypic antibody directed against its antigen binding site.

Thus the analyte (and analogue) preferably constitutes a specific binding pair with the binding site of the binding agent.

The term specific binding pair is used to describe a pair of molecules comprising a specific binding member (sbm) and a binding partner (bp) therefor which have particular specificity for each other and which in normal conditions bind to each other in preference to binding to other molecules. Examples of specific binding pairs are antigens and antibodies, ligands (such as hormones, etc.) and receptors, avidin/streptavidin and biotin, and complementary nucleotide sequences. The skilled person will be able to think of many other examples and they do not need to be listed here.

Further, the term "specific binding pair" is also applicable where either or both of the specific binding member and binding partner comprise just the binding part of a larger molecule. Thus in the context of antibodies, a specific binding member may comprise just a domain of an antibody (antibody binding domain) which is able to bind to either an epitope of an antigen or a short sequence which although unique to or characteristic of an antigen, is unable to stimulate an antibody response except when conjugated to a carrier protein.

Where the reporter molecule is capable of binding to the reporter site, the affinity of the reporter molecule for binding agent/analyte complexes is at least 10 fold greater than for binding agent/analyte analogue complexes, preferably greater than 20 fold, preferably greater than 50 fold, and more preferably greater than 100 fold.

Preferably the reporter molecule is specific for the reporter site, and constitutes a specific binding pair with it in the same manner as described above for analyte/analogue and binding site, mutatis mutandis.

Binding Agents

The binding agent will typically be a protein, but may be any binding agent, including molecular imprints (mips) or aptamers.

Examples of suitable binding agents include enzymes having the analyte as a substrate or modulator. Examples of modulators include inhibitors and activators, either competitive or allosteric, which may exert their physiological effects by binding to the active site or elsewhere on the enzyme molecule. Where the analyte is a substrate for the enzyme, the enzyme may be inactivated, so that the enzyme does not structurally alter or modify the analyte and so compromise the assay. This may be achieved by mutagenesis (e.g. of a catalytically important residue at the active site), by removal of a cofactor, etc. Alternatively the enzyme may be unable to act on the analyte because of the absence in the assay medium of another required molecule such as a cosubstrate.

Further examples of binding agents include molecules having a physiological binding function, such as lectins, receptor molecules and binding proteins, e.g. vitamin binding proteins such as folate binding protein, etc.

Further preferred binding agents are immunologically significant molecules such as antibodies, T cell receptors, MHC molecules etc., with antibodies being particularly preferred. Thus the analyte binding site is preferably the antigen binding site of an antibody.

Molecular imprints may also be used as binding agents. These may be made by forming a plastic polymer around a target analyte, extracting the analyte from the formed polymer, and then grinding the polymer to a fine powder, as described in Nonbiological Alternatives to Antibodies in Immunoassays; Principles and Practice of Immunoassay (second edition) Chapter 7 pp 139-153 Ed CP Price & DJ Newman (1997).

Aptamers are DNA or RNA molecules, selected from libraries on the basis of their ability to bind other molecules. Aptamers have been selected which can bind to other nucleic acids, proteins, small organic compounds, and even entire organisms.

The binding agent is preferably monovalent. This ensures that chemical modification does not result in modified binding agent molecules correctly modified adjacent some binding sites but inappropriately modified adjacent others.

Antibodies

It has been shown that fragments of a whole antibody can perform the function of binding antigens. The term "antibody" is therefore used herein to encompass any molecule comprising the binding fragment of an antibody, and the term binding agent and binding site should be construed accordingly. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988). In preferred embodiments the binding agent comprises a single antigen binding site specific for the analyte, i.e. a monovalent antibody or antibody fragment.

Bispecific antibodies are also specifically contemplated for use in the present invention (see below).

Modification of the Binding Agent The binding agent may be modified by any suitable method to create the reporter site.

In preferred embodiments, the reporter site may be created by mutagenesis (e.g. site directed mutagenesis) of the binding agent to introduce a peptide sequence not naturally occurring in the molecule. Such a sequence may provide an epitope for an antibody, or may be known to bind to another molecule suitable for use as a reporter molecule in the assay methods described herein. The sequence may be a known epitope for a pre-existing antibody, such as the FLAG epitope tag.

Alternatively an antibody may be raised against the peptide sequence or against the modified binding agent, e.g. by immunising a suitable mammal with the modified binding agent. Preferably the immunised animal will be tolerant to the unmodified binding agent, so that antibodies are preferentially raised against the reporter site. This may be achieved by raising the antibodies in the species from which the binding agent is originally derived. It should be noted that mutagenesis need not introduce a large number of new residues. A single mutation (e.g. deletion, insertion or substitution of a single amino acid residue) may be sufficient to provide a novel epitope on the surface of a molecule. Mutagenesis may also create a novel glycosylation site not present on the parent molecule. Expression in eukaryotic cells will result in addition of carbohydrate not present on the parent molecule, which may serve as a reporter site.

Preferably mutagenesis is performed at a region of the binding agent which is tolerant to mutagenesis. By this is meant that the affinity of the binding agent for the analyte is not significantly reduced; preferably the reduction in affinity is less than one order of magnitude.

The preferred location will clearly depend on the nature of the binding agent, but in general surface loops of the molecule which are flexible and have no defined conformation (e.g. do not have alpha helical, beta strand or beta turn configuration) and do not form part of the binding site for the analyte will often be suitable. For example suitable regions of an antibody for modification are the framework regions in the Fv region close to the antigen binding site.

Modification by mutagenesis is not restricted to the introduction of short peptide epitopes and the like into the binding agent. It may also extend to the generation of fusion proteins comprising the binding agent and a subunit or portion of another protein. For example, epitopes of the fusion partner may form the reporter site. Alternatively the fusion partner may itself have a biological binding function for a specific binding partner as described above for the binding agent itself, e.g. it may be a receptor, enzyme or antibody capable of binding to a particular ligand, substrate or cognate antigen.

Binding of the analyte analogue to the binding agent may prevent the fusion partner from binding to its specific binding partner. That part of the fusion partner which binds its specific binding partner may therefore be regarded as the reporter site, and the specific binding partner itself may therefore be regarded as the reporter molecule.

Thus it will be seen that the binding agent may comprise a bispecific antibody; this aspect of the invention will be described in more detail below.

Further preferred techniques include chemical coupling of a labelling reagent to the binding agent, preferably to the surface of the binding agent, so that the residue of the labelling reagent (which may be referred to as a label) serves as the reporter site for binding of the reporter molecule. Typically the label will be coupled to an amino acid side chain of the binding agent. Any suitable coupling chemistry may be used, depending upon the identity of the target side chain.

In order for the modified binding agents to be suitable for use in the assay methods described, it is important that the label is introduced only at a site which can be blocked by binding of the analyte analogue to the binding agent, but not by binding of analyte itself. Preferably there should be no label present on the binding agent to which the reporter molecule can gain access when analyte analogue is bound. Thus the choice of the site will be determined by the identity of the binding agent, analyte, analyte analogue and reporter molecule.

Preferably the labelling reagent is targeted to an amino acid residue of a type only present at one location accessible to the coupling reaction, e.g. a unique amino acid residue, i.e. a residue of a type not found elsewhere in the binding agent molecule. Such a residue may be introduced into the binding agent by mutagenesis (e.g. site directed mutagenesis). For example, a cysteine residue may be introduced into a molecule otherwise lacking cysteine, or alternatively into a molecule in which all other cysteines participate in disulphide bond formation in the folded molecule, to provide a free sulphydryl group suitable for coupling (e.g. to biotin maleimide).

The label may be any moiety capable of interacting with (e.g. binding to) the reporter molecule. Many specific binding pairs used conventionally in biological assays can therefore be used as label and reporter molecule, such as an epitope with its cognate antibody (as described above, whether the epitope is a peptide, hapten or other antigenic determinant), biotin with avidin/streptavidin or an anti-biotin antibody, a carbohydrate with a lectin, complementary nucleic acids, etc. Particularly preferred is biotin in combination with an anti-biotin antibody, IgM antibodies being particularly preferred.

As described above, other molecules having binding functionalities can also be used to form the reporter site. Any such molecule or portion or domain of a molecule which could be incorporated into a fusion with the binding agent can typically be chemically linked to the binding agent. Thus also included as potential labelling moieties are the antibodies, receptors, binding proteins, enzymes, etc. already mentioned supra, where binding of the reporter molecule to the reporter site can be prevented by binding of analyte analogue to the binding agent.

The particular coupling chemistry used will depend upon the nature of the binding agent and the labelling reagent—see e.g. Bioconjugate Techniques by Greg T. Hermanson, Academic Press 1996 (ISBN 0-12-342335-X). Coupling may be effected by use of a conventional coupling reagent, such as those conventionally used in the art to join antibodies to enzymes. Suitable reagents include aldehydes such as glutaraldehyde and other heterobifunctional reagents such as described in Chemistry of Protein Conjugation and Cross-Linking by Shan S. Wong, CRC Press 1991, for example: N-Succinimidyl3-[2-pyridyldithiolpropionate) (SPDP); (m-Malcimidobenzoyl N-hydroxysuccinimide ester) (MBS); (Succinimidyl 4-(N-maleimidomethylN-cyclohexanel-carboxylate) (SMCC); (N-Hydroxysuccinimdyi-2,3-dibromoproprionate) (SDBP); (1,5-Difluoro-2,4 dinitrobenzene) (DFDNB); (Bis-([3-(4-Azidosalicylamido) ethyl] disulphide) (BASED).

It is also possible to use a targeted labelling reagent in order to target the label to a particular portion of the binding agent.

A suitable labelling reagent may have at least a reactive group and a targeting moiety capable of binding reversibly to a selected targeting site on the binding agent. The reactive group is typically capable of reacting with a specific amino acid side chain under given conditions. Suitable choice of spacer group between these two functionalities will determine the distance from the targeting site at which the reactive group can react, and hence the distance from the targeting site at which the labelling reagent can become bound to the binding agent.

Preferably the labelling reagent is targeted to a location close to the binding site for the analyte. In such embodiments, the targeting moiety is preferably the analyte itself, or a fragment or mimetic thereof capable of being recognised and bound by the binding site of the binding agent.

Thus broadly there is provided a method of modifying a binding agent for use in an assay as described herein, comprising the steps of:
(a) forming a complex between said binding agent and labelling reagent, the labelling reagent comprising a targeting moiety capable of reversible association with a targeting site on the binding agent, and a reactive group; causing the reactive group to react with the binding agent; and causing the targeting moiety to dissociate from the binding agent.

By suitable choice of targeting group, this method can be applied to any binding agent suitable for use in the assays described herein. In particular any binding agent having an analyte binding site as described in this specification and suitable for use in assays as described herein may be modified in this way by use of the analyte or a mimetic thereof as the targeting moiety.

The invention further provides a method of labelling a binding agent having an analyte binding site, comprising the steps of:
forming a complex between said binding agent and a labelling reagent, the labelling reagent comprising a targeting moiety capable of binding the analyte binding site, and a reactive group, wherein said complex is formed by binding of said targeting moiety to said binding site; causing the reactive group to react with the binding agent; and causing the targeting moiety to dissociate from the binding agent.

Depending on the nature of the reactive group of the labelling reagent, the reaction between the binding agent and the reactive group of the labelling reagent may be initiated by irradiation, change in pH or temperature, addition of oxidising or reducing agents, etc. In preferred embodiments the reactive group is a photoactivatable moiety, e.g. an aryl phenyl, aryl azide, perfluorinated aryl azide, benzophenone or diazo group.

The targeting moiety and reactive group of the labelling reagent are typically coupled by a flexible linker group. When the analyte moiety is associated with the binding site of the binding agent, the linker group should be sufficiently flexible to allow the reactive group to gain access to groups on the surface of the binding agent with which it is capable of reacting, while being short enough to ensure that the modified binding agent is still of use in the assays described herein. That is to say, the label must be coupled close enough to the binding site that it cannot interact with a reporter molecule when analyte analogue is bound to the binding site in an assay for analyte. The linker may comprise a hydrocarbon chain, an aliphatic, heteroaliphatic, aromatic or heteroaromatic chain, a polymeric chain or a polypeptide or nucleic acid chain.

The targeting moiety of the labelling reagent may subsequently be derivatised to prevent it interacting further with the binding site and blocking interaction between the binding site and analyte in an assay.

Alternatively the targeting moiety may be cleaved from the labelling reagent, either before or after dissociation from the binding site. Thus a selectively cleavable group may be located between the targeting moiety and the reactive group, typically within the linker group described above.

Depending on the nature of the selectively cleavable group, it may be cleavable by irradiation, change in pH or temperature, addition of oxidising or reducing agents, etc. Preferably the conditions required for cleavage of the selectively cleavable group are different to those required for initiation of the reaction between the reactive group and the binding agent. In preferred embodiments the selectively cleavable group is cleavable by reduction or irradiation (a photocleavable group, such as a 1-(2-nitrophenyl)-ethyl moiety. In particularly preferred embodiments, especially where the reactive group is a photoactivatable moiety, the selectively cleavable group is a disulphide bond.

The labelling reagent may further comprise a label moiety. The derivatised targeting moiety may be considered a label moiety, as may the residue of the labelling reagent after release of the analyte/mimetic through cleavage of a selectively cleavable group.

Alternatively, a further label moiety may be coupled to the labelling reagent after the labelling reagent has been coupled to the binding agent. The label moiety may be coupled to the labelling reagent via a group generated by cleavage of said selectively cleavable group, or the labelling reagent may possess a further reactive group, distinct from the selectively cleavable group, to facilitate such coupling of a label moiety. The function of the label moiety is to serve as (at least part of) the reporter site; any group capable of serving as a reporter site as described in this specification may therefore constitute a label moiety.

The binding agent may be e.g. an antibody or an enzyme. Where the binding agent is an antibody, the targeting moiety of the labelling reagent may comprise the cognate epitope of said antibody.

Where the binding agent is an enzyme, the targeting moiety of the labelling reagent may comprise a substrate or modulator of said enzyme. Particularly where the analyte is a substrate for the enzyme, the enzyme may be inactivated, so that the analyte can bind to the active site without being chemically modified by the enzyme.

This method is particularly appropriate for modifying antibodies, wherein the antigen binding site of the antibody serves as the targeting site, and its cognate epitope serves as the targeting group of the labelling reagent.

Thus there is further provided a method of modifying an antibody having a binding site for an epitope of a cognate antigen, comprising the steps of
(a) forming a complex between said antibody and a labelling reagent, the labelling reagent comprising said epitope of the cognate antigen or a mimetic thereof and a reactive group having a selectively cleavable group therebetween;

(b) causing the reactive group to react with the antibody;
(c) selectively cleaving the selectively cleavable group; and
(d) causing the epitope or mimetic to dissociate from the antibody.

The method may comprise the further steps of using the modified binding agent so generated in an assay of the type described herein.

Reaction between the reactive group and the binding agent may take place in the presence of a quencher substance to reduce unwanted binding of active species away from the desired area of conjugation. Alternatively, the labelling reagent may be incubated with the binding agent, and free excess labelling reagent subsequently separated from the binding agent-labelling reagent complexes before the reaction between the two molecules is initiated. Separation may be performed for example by rapid size-exclusion column chromatography or dialysis.

After reaction, it is useful, but not essential, to remove any unreacted (and hence unmodified) binding agent, and/or binding agent modified by conjugation at an inappropriate site. Unreacted binding agent can be removed e.g. by purification on an affinity column bound with reporter—unmodified binding agent will not bind the reporter and may be removed before retrieving the bound changed material. Inappropriately modified binding agent can be removed by mixing the reaction mixture with analyte analogue and running it again through the reporter affinity column—suitably conjugated material will pass through whereas molecules with an inappropriately bound moiety will not.

It is preferable that the binding agent is univalent, so that different binding sites are not modified in different ways, leading to a reduction in effectiveness of the reagent.

U.S. Pat. No. 5,532,379 (Fujimoto) describes trifunctional reagents which may be used as the backbone for the labelling reagents used in these methods. As described therein, these reagents are trifunctional compounds comprising a biotin moiety, an NHS (N-hydroxysuccinimido) active ester and a photoactivatable aryl azide, each dependent from a central CH group. Linker groups comprising disulphide bonds are present between the central CH group and at least one of the NHS ester and the aryl azide.

As applied to the present invention, the targeting moiety may be linked to the trifunctional backbone via the reactive NHS group. A disulphide bond, or other suitable selectively cleavable group, is located between the central CH group and the targeting moiety, but not between the CH group and the aryl azide group, which serves as the reactive group. Thus the compound Sulfo-SBED (sulfosuccinimidyl-2-[6-(biotinamido)-2-(p-azidobenzamido)-hexanoamido]ethyl-1,3'-dithiopropionate- commercially available from Pierce and Warriner, product no. 33033) as described in U.S. Pat. No. 5,532,379 is particularly appropriate for use in such methods.

A similar compound lacking the biotin functionality could be used as a bifunctional molecule for application in the labelling methods described above. After reaction of the aryl azide with the binding agent and release of the targeting moiety by cleavage of the diulphide bond, a label may be conjugated to the free thiol thus formed to be used as a reporter group. Alternatively the residue of the molecule could serve as a reporter group. An antibody raised against the remaining portion of the molecule could be used as a reporter molecule.

In use, the labelling reagent is incubated with the binding agent so that they become associated via the targeting moiety and targeting site. Stoichiometrically equivalent amounts may be used, but if excess labelling reagent is used it may be removed from the system by suitable separation techniques such as preparative HPLC.

The aryl azide is induced to react with the binding agent by irradiation, covalently linking the labelling reagent to the binding agent. The selectively cleavable group is then cleaved (e.g. a disulphide bond is reduced by treatment with dithiothreitol or beta-mercaptoethanol) to separate the targeting moiety from the rest of the complex and enable it to be removed after dissociation from the binding agent by, for example, simple dialysis or size exclusion chromatography, optionally employing a dissociator such as a chaotropic agent or conditions.

The biotin moiety described in U.S. Pat. No. 5,532,379 may be used as the labelling moiety, or any other suitable labelling moiety may be used instead. Alternatively a further reactive group may be included as part of the trifunctional backbone and a suitable labelling moiety added after the labelling reagent has been covalently linked to the binding agent. As a further alternative, this functionality may be omitted from the labelling reagent and a labelling moiety introduced after the labelling reagent has been covalently linked to the binding agent via the now free group (e.g. a sulphydryl group) generated on release of the targeting moiety by cleavage of the selectively cleavable group.

Mimetics of the analyte or epitope may be designed by any appropriate method. Typically, the particular parts of the analyte or epitope that are critical and/or important in determining binding to the binding agent are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the analyte or epitope and the binding agent are modelled. This can be especially useful where the analyte/epitope or binding agent change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise while retaining its binding properties, and any other desirable features depending on the individual method to be used in labelling. The mimetic or mimetics found by this approach can then be screened to see whether they have the required property, or to what extent they exhibit it. Further optimisation or modification can then be carried out to arrive at one or more final mimetics for use.

Bispecific Antibodies

As already described, the binding agent may be an antibody (as defined above), and preferably comprises only a single antigen binding site specific for the analyte.

In preferred embodiments the reporter site is formed by, or is part of, the antigen binding site of an antibody specific for the reporter molecule. The binding agent therefore comprises a molecule having antigen binding sites for both the analyte and reporter molecule, i.e. a bispecific antibody.

Thus there is further provided a method of determining an analyte in a sample, comprising contacting the sample with (i) an antibody having a first antigen binding site capable of binding either said analyte or an analyte analogue, and a second antigen binding site capable of binding a reporter molecule;
(ii) said analyte analogue; and
(iii) said reporter molecule;
wherein said second antigen binding site is capable of binding the reporter molecule when the first antigen binding site is bound to analyte, but not when the first antigen binding site is bound to analyte analogue,
and optionally determining the amount of reporter molecule bound to the second antigen binding site.

It will be clear from the foregoing that the reporter molecule is other than the analyte or analyte analogue.

Suitable binding agents therefore include bispecific single chain Fv dimers (PCT/US92/09965) and "diabodies", i.e. multivalent or multispecific fragments constructed by gene fusion (WO94/13804; P. Holliger et al., Proc. Natl. Acad. Sci. USA 90 6444-6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (eg by a peptide linker) but unable to associate with each other to form an antigen binding site: antigen binding sites are formed by the association of the first domain of one polypeptide within the multimer with the second domain of another polypeptide within the multimer (WO94/13804).

Conventional bispecific antibodies can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above.

An antibody of one specificity may be chemically coupled to another antibody of another specificity by any of the wide variety of chemical means available for such coupling (such as glutaraldehyde, or preferably, one of the many more specific cross linkers such as SPIDP—(N-Succininimidyl-3-(2-pyridyldithioI propionate). Suitable methods for the production of bispecific antibodies are described by H. Paulus, Behring Inst. Mitt., 78,118-132, 1985. Small antibody fragments have particular advantages and may be prepared as described by Holliger et al., Proceedings of the National Academy of Sciences of the United States of America, 90(14):6444-6448; 1993). When chemical linking of antibody fragments containing binding sites produces a mixture which contains useful conjugates these can be purified away from non-useful conjugates. Bispecific antibodies may also be usefully prepared by means of solid phase synthesis as described in DeSilva & Wilson, Journal of Immunological Methods, 188 (1995), 9-19.

Alternatively, bispecific antibodies may be prepared by separating the chains of the antibodies and allowed to recombine with each other, some chains thereby combining with chains of the other antibody forming bispecific antibodies (Paulus, Behring Inst. Mitt., 78,118-132, 1985; Lebegue et al., C.R. Acad. Sci. Paris, Seric Ill, 310:377-382, 1990).

Bispecific antibodies may also be usefully prepared by the formation of quadromas from the two hybridomas synthesising the two antibodies from which a bispecific antibody is required (Suresh et al., Methods in Enzymology, 121, 211, 1986; Bos R, Nieuwenhuitzen W, Hybridoma, 11(1):41-51, 1992) producing the two antibodies desired to be present in the complex gives a mixture of desired antibodies and contaminants which can be removed. De Lau et al, Journal of Immunological Methods (1989) 117, 1-8 describes a suitable system for the production based on the formation of HAT-s-neomycin-r double mutants.

Alternatively, recombinant conjugates between antibody binding regions may be formed by genetic recombinant means such as described in COS-1 cells for the production of a bifunctional murine:human chimeric antibodies (De Sutter & Flers, Molecular Immunology, 31(4)261-267 may also be employed.

It may be preferable to use scFv dimers or diabodies rather than whole antibodies. Diabodies and scFv can be constructed without an Fc region, using only variable domains. Other forms of bispecific antibodies include the single chain "Janusins" described in Traunecker et al, Embo Journal, 10, 3655-3659, (1991).

Bispecific diabodies, as opposed to bispecific whole antibodies, are also particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Analytes

The analyte may be a medicament, drug of abuse, hormone, pollutant, diagnostic marker or any other compound in need of analysis, including metabolites of the above. Frequently the analyte will be a small molecule of less than about 15000 daltons.

Thus analytes which can be determined by this invention include drugs, including drugs of abuse, such as alkaloids including morphine alkaloids, such as morphine, codeine, heroin, dextromethorphan and methadone; cocaine alkaloids such as cocaine and benzyl ecgonine; ergot alkaloids such as lysergic acid; steroid alkaloids; iminazoyl alkaloids; quinoline alkaloids and diterpine alkaloids; ecstasy and its derivatives; marijuana including cannabinol and tetrahydrocannibinol and synthetic agents such as DIVIDE.

Further analytes include medicaments including antibiotics such as penicillin, chloromcetin, actinomycetin, tetracycline and their metabolites and derivatives, cardiac glycosides such as digoxin, peptide and steroidal hormones and other metabolic products such as thyroxine and triiodothyronine and steroids such as oestrogens, e.g. oestradiol and oestrone-3-glucuronide, other steroids such as progesterone and androgens such as testosterone, and renocortical steroids, bile acids, cardiotonic glycosidases and aglycones, saponins and saponin derivatives; pteridins such as neopterin; peptides such as vasopressin; and immunosuppresants such as cyclosporin, FK506, and mycophenolic acid.

A further class of analytes include vitamins such as A, B, e.g. B12, C, D, E, biotin and K, folic acid, niacin and thiamine; food toxins including bacterial and fungal toxins such as aflatoxin.

A further class of analytes include pollutants including environmental and agricultural interest such as PCB and aflatoxin; pesticides such as polyhalogenated biphenyls, phosphate esters, thiophosphates, carbamates, polyhalogenated sulphenamides and their derivatives; poisons and household toxins. Within this, compounds generated from industrial processes such as petrochemical activity are a group of important analytes.

Analyte Analogue

The analyte analogue may be any molecule or molecular complex which can prevent binding of the reporter molecule to the reporter site when bound to the analyte binding site in place of analyte. This will normally be achieved by steric means, in which the analyte analogue physically blocks access of the reporter molecule to the reporter site. However other modes of action are possible. For example, if the reporter molecule is charged, then the analyte analogue may carry the same charge and so prevent the reporter binding by electrostatic repulsion.

Analyte analogues are therefore typically large molecules comprising the analyte, a fragment or portion thereof sufficient to exhibit the same interactions with the analyte binding site, or a mimetic of the analyte, conjugated to a carrier, which may be a single molecule, such as bovine or human serum albumin, keyhole limpet haemocyanin, or a bead or particle, formed e.g. from gold or latex. Their size will clearly depend on the size of the analyte itself, and the nature of the binding agent, reporter site and reporter molecule, but typically they may have a molecular weight of 50,000 to many millions, and preferably 60,000 to 600,000 daltons. Mimetics of the analyte molecule may be generated as described above, mutatis mutandis.

Reporter Molecules and Detection Methods

Numerous methods exist by which the interaction between the reporter molecule with the binding agent may be detected. The reporter molecule may be directly or indirectly labelled (e.g. with radioactive, fluorescent chemiluminescent or enzyme labels) so that it can be detected using techniques well known in the art. Directly labelled reporters have a label associated with or coupled to the molecule. Alternatively the reporter may be detectable via a further labelled species (e.g. a labelled antibody capable of binding to the reporter) or may act on a further species to produce a detectable result. Thus, radioactive labels can be detected using a scintillation counter or other radiation counting device, fluorescent labels using a laser and confocal microscope, and enzyme labels by the action of an enzyme label on a substrate, typically to produce a colour change. After the binding reaction and any necessary separation step has taken place, the result of the assay is obtained by contacting the enzyme with a substrate on which it can act to produce an observable result such as a colour change, the extent of which depends on the amount of analyte originally in the sample. Suitable enzyme labels may give rise to detectable changes such as colorimetric, fluorometric, chemiluminescent or electrochemical changes, and include horseradish peroxidase and alkaline phosphatase, as well as lysozyme (detectable for example by lysis of organisms such as microccocus lysodeikticus), chymotrypsin, and $E.\ coli.$ DNA polymerase.

Alternatively as described above, the reporter site may be a part of an enzyme, in which case the reporter molecule may be a substrate molecule or a molecule capable of binding to the enzyme such as an allosteric activator or inhibitor, as long as access of the reporter to the appropriate portion of the enzyme is restricted by the analyte analogue. Thus the reporter may simply bind to the enzyme, in which case it may be detected as described above, or may constitute a substrate for the enzyme, in which case a detectable change (e.g. a colour change) may result from enzyme activity on the substrate.

Alternatively the reporter site may comprise a cofactor or prosthetic group such as FAD or NAD for an enzyme. The apoenzyme may then be used as the reporter molecule. Binding of the apoenzyme to its cofactor provides a catalytically active enzyme which may act on a substrate to produce a detectable signal. For example, FAD may be used as the reporter site, with glucose oxidase or amino acid oxidase as the reporter molecule. See, e.g. U.S. Pat. No. 4,622,293.

When the binding agent is a bispecific or bivalent antibody (i.e. the reporter site is an antigen binding site) the reporter molecule will typically be the cognate antigen. Binding can be detected as described above. Alternatively the reporter may be an anti-idiotypic antibody.

Other methods may also be used to detect interaction between binding agent and reporter molecule, including physical methods such as surface plasmon resonance, agglutination, light scattering or other means.

Any method known in the art for separately conjugating a label to a reporter molecule may be employed, including those methods described by Hunter et al, Nature 144:945, 1962; David et al, Biochemistry 13:1014, 1974; Pain et al, J. Immunol. Meth. 40:219, 1981; and Nygren, J Histochem. and Cytochem. 30:407, 1982. One favoured mode is by covalent linkage with an individual fluorochrome, phosphor or laser dye with spectrally isolated absorption or emission characteristics. Suitable fluorochromes include fluorescein, rhodamine, luciferin, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors.

In homogeneous assay formats, the binding agent which has bound analyte and then bound to the reporter molecule can be detected by plasmon resonance or in an immunoprecipitation assay, see Zola, Monoclonal Antibodies: A Manual of Techniques, 147-158 (CRC Press, Inc, 1987). The signal generation methods described in The Immunoassay Handbook (Second Edition) Ed D Wild published by the Nature Publishing Group (2001) are also appropriate. Of particular application are those homogeneous systems described in Chapter 11 (E. F. Ullman). Scintillation Proximity Assay (SPA) (with for example a weak alpha or beta-emitter and a fluorophore) and Enzyme Channelling (with for example glucose oxidase and peroxidase) provide particularly attractive systems for use in the methods described. In these methods the binding agent and reporter may each be labelled with complimentary components of the detection system such that when analyte is bound the two components may be brought closely enough together to produce a detectable signal but when analyte analogue is bound no such association occurs and thus no signal is produced.

The reporter may be an antibody which binds a ligand which produces a different signal depending on whether or not it is bound to the antibody. Suitable ligands of this kind include those which show a difference in absorption of production of electromagnetic radiation (in particular visible and UV light and fluorescence) depending on whether the ligand is bound or unbound. Preferred ligands for use in this aspect of the invention include fluorophores such as fluorescein and rhodamine.

Kits

The modified binding agents described herein may be packaged into kits for use in assays to determine analyte in samples, e.g. biological samples. There is thus provided a method of preparing a kit for use in determining an analyte in a sample, comprising (a) modifying a binding agent having an analyte binding site capable of binding either said analyte or an analyte analogue, said modification comprising creating a reporter site adapted to interact in a detectable manner with a reporter molecule when the modified binding agent is bound to analyte, but not when the modified binding agent is bound to analyte analogue; and (b) packaging together
(i) said modified binding agent;
(ii) said reporter molecule; and
(iii) said analyte analogue.

The reporter molecule may be capable of binding to the reporter site.

The kit may also comprise the step of co-packaging (iv) said analyte, which may be useful in preparing a standard curve for calibration of the assay, and/or (v) instructions for use of said kit to determine the analyte in a sample.

Also provided is a kit as obtainable by, and for use in, the methods described herein.

When the binding agent is a bispecific antibody comprising two antigen binding sites, each specific for one of the analyte and the binding agent, there is provided a kit for use in determining an analyte in a sample comprising (i) an antibody having a first antigen binding site capable of binding said analyte or an analyte analogue and a second antigen binding site capable of binding a reporter molecule, (ii) said analyte analogue, and (iii) said reporter molecule, wherein said second antigen binding site is capable binding the reporter molecule when the first antigen binding site is bound to analyte, but not when the first antigen binding site is bound to analyte analogue.

Solid Phase Assay Systems

The assay systems described herein have the advantageous feature that the signal increases as the analyte concentration increases in the sample. This helps to avoid the problematic separation steps used in other systems to separate populations of label-containing species, and limitations on the use of excess amounts of labelled reagents (U.S. Pat. Nos. 4,670,383 and 5,798,273).

As a result, the assays are especially suitable for use in solid phase systems, such as lateral flow strip or dip-stick assay devices (as described e.g. by Price et al., Disposable Integrated Immunoassay Devices; Chapter 22 of Principles and Practice of Immunoassay, 2nd edn, 1997, Christopher P Price and David J Newman eds., Macmillan Reference Ltd, Basingstoke, UK (ISBN 1-56159-145-0)), or on a micro-scale in, for example, such applications as lab-on-a-chip type array devices.

Thus either the modified binding agent or the reporter molecule (or an agent capable of binding to a binding agent/reporter complex) may be immobilised on a solid phase.

In some embodiments, the non-immobilised component (reporter molecule or modified binding agent) may be directly or indirectly labelled as described above. In one example, the non-immobilised component is directly or indirectly bound to a visibly detectable label such as a gold particle.

In some embodiments, the binding agent is immobilised on solid phase, preferably in a discrete location such as a band or spot. Multiple binding agents can be immobilised on one support for carrying out a plurality of assays simultaneously. In alternative embodiments, the binding agent is immobilised on a solid support, e.g. in a detection zone, and the reporter is present in the assay free in solution or able to migrate on a solid support.

EXAMPLES

The following Examples are provided by way of illustration only.

Example 1

Development of a Digoxin Immunoassay System

The following standard buffers were employed:
R—50 mM Tris 0.2% BSA pH 7.4.
CB—coating buffer –50 mM bicarbonate buffer pH 9.3.
TT—50 mM Tris pH 7.4 containing 0.2% TWEEN 20.
P—0.1M phosphate buffer pH 7.5 containing 0.1M NaCl.

Preparation of Fab Fragments:

One mg of a monoclonal antibody against digoxin and 1 mg of a monoclonal antibody to fluorescein isothiocyanate (Biogenesis U.K. cat no 4510-7914 were both individually treated with Ficin antibody fragmentation kit of Pierce and Warriner (UK) Ltd (cat no. 44880) to obtain Fab fragments of the antibodies.

Preparation of the Bispecific Fab Conjugate:

The Fab fragments of the monoclonal antibodies against digoxin and fluorescein were taken and combined together to form a bispecific reagent as follows:

The anti-digoxin and anti-fluorescein Fabs were adjusted to 0.1 mg/ml buffer. One ml of each was dialysed in 1 liter of buffer P for 2 hours. They were then placed into Eppendorf tubes. The cross-linker, (N-Succinimidyi-3[2-pyridyldithio]propionate) (SPDP) (Pierce & Warriner cat. no. 21657) was dissolved to make a fresh solution at a concentration of 0.63 mg/ml in pure ethanol. Ten µl of this solution was added to each Fab preparation with mixing. The mixtures were then allowed to stand for 10 minutes.

The anti-fluorescein Fab mixture was then dialysed overnight at 4° C. in buffer P. The anti-digoxin Fab mixture was dialysed in 0.1 M acetate buffer pH 4.5 overnight at 4 C and was then activated by the addition of 100 µl of 0.5M dithiothreitol (Sigma Chemical Co Ltd. cat. no. D5545) and then allowed to stand for 30 minutes at room temperature. The reduced Fab preparation was then dialysed against buffer P (2×2 liters, 2 hours each time). The Fab preparations were then mixed together and left to react for two days. The bispecific antibody preparation was then dialysed overnight against distilled water. The volume of the conjugate was then 3.5 ml.

Purification of Suitable Bispecific Conjugates 0.3 mg of dialysed digoxin BSA (such as 0.3 ml of a 1 mg/ml solution) was then added to the bispecific conjugate mixture and incubated at RT for 30 minutes. The mixture in buffer R was passed through a fluorescein SEPHAROSE column prepared from EAH-SEPHAROSE (Pharmacia LKB, Sweden) as follows: 10 ml of the EAH-SEPHAROSE beads as supplied were washed in 0.1 M bicarbonate buffer pH 9.3 after which 1 ml of a solution of 1 mg/ml fluorescein isothiocyanate (Sigma Chemical Co Ltd cat number F4274) was added slowly at 100 µl time. The mixture was left gently shaking overnight at room temperature, covered in foil. The following day the column was made and washed with the 0.1 M bicarbonate buffer, followed by buffer R. The column was first used with a preparation of the conjugate as above but without BSA added to the elution buffer. For the present preparation, the elution buffer contained BSA as described above. One ml fractions of the eluate were collected, the first two after the application of the sample being ignored and the subsequent four fractions being collected and combined. The volume of the bispecific conjugate (BC) is made up to 5 ml with buffer R.

A Nunc microtitre plate was prepared by coating it with 200 μl/well BSA-fluorescein (Sigma Chemical Co Ltd cat, no. A 9771) 10 μg/ml in coating buffer and leaving it overnight at room temperature. The plate was then glazed with coating buffer containing 0.2% BSA and left for 10 mins at RT after which it was washed four times with TT. Triplicate wells then received 100 μl of the following digoxin standards in TT buffer: 1 μg/ml; 100 ng/ml; 10 ng/ml; 1 ng/ml; 0.1 ng/ml; 0 standard. With mixing, each well of a series then received 10 μl of BC, followed by 90 μl R. The plate was incubated for one hour at RT and then washed in TT. 200 μl of a 1:1000 dilution of anti-mouse IgG Fab labelled with alkaline phosphatase (Sigma Chemical Co Ltd, cat. no. A 2179 was added and left for 30 minutes at RT. The plate was washed four times with TT, 200 μl of pNPP was added and the reaction monitored at 405 nm until the fastest developing wells had reached the limit of the spectrophotometer.

The data obtained was as follows:

|         | Digoxin (ng/ml) | | | | | |
|---------|-----|------|------|------|------|------|
|         | 0.0 | 0.1 | 1.0 | 10 | 100 | 1000 |
| Abs 405 | 1663 | 2067 | 2246 | 2236 | 2626 | 2665 |

From these data a standard curve was drawn up to determine digoxin concentrations in unknown samples.

Example 2

Determination of Fluorescein

The bispecific antibody of Example 1 was made as in Example 1, and in analogous manner to Example 1, purified via a digoxin column with in the presence of fluorescein-BSA. Again, in analogous fashion, a standard curve for fluorescein was generated employing microtitre plates coated with digoxin-BSA and employing as hapten analogue fluorescein-BSA. The presence of the bispecific antibody on the plate was determined by the addition of an alkaline phosphatase-labelled anti-immune complex antibody for the digoxin Fab part of the bispecific antibody. Again, in analogous fashion, after suitable incubation excess labelled antibody was washed away, substrate added and a standard curve obtained against which samples containing unknown concentrations of fluorescein could be determined.

Example 3

Determination of Gentamicin

Example 1 was repeated changing the digoxin monoclonal antibody for a monoclonal antibody against gentamicin (Biogenesis Ltd, U.K., Cat. No. 4630-0206). The digoxin BSA was also replaced by gentamicin-BSA (Biogenesis Ltd., England, number 46300604). A standard curve was obtained against gentamicin enabling unknown samples to be analysed for gentamicin.

One mg of a monoclonal antibody against gentamicin was used to prepare Fab fragments using the Pierce Immunopure IgG1 Preparation Kit. Fab fragment were obtained of 0.2 mg/ml. The Fab fragment preparation was diluted to 0.1 mg/ml to be conjugated to anti-FITC Fab fragment also at 0.1 mg/ml. 2.0 ml of this conjugate of gentamicin and FITC was added to 0.25 ml of a 1 mg/ml solution of gentamicin BSA (previously dialysed). It was left at room temperature for 30 minutes.

A column (5 ml) of SEPHADEX-FITC was prepared and equilibrated with 50 mM Tris buffer containing 0.2% BSA. 0.75 ml of the above gentamicin-BSA was run through the column, again using Tris/BSK 1 ml of the conjugate/gentamicin-BSA mixture was applied to the column eluted in Tris/13 SA. 1 ml aliquots were collected and the optical densities measured to determine the sample peak. This material was then used as follows:

(i) An ELISA plate was coated with Fab specific anti-IgG (10 μg/ml). After blocking and washing the plate, 50 μl of conjugate (10 μg/ml) was added plus 50 μl of a standard solution of gentamicin from 100 μg/ml to 100 μg/ml (in ten-fold steps). 20 μl of alkaline phosphatase-FITC was added. The plate was incubated at 3 C for 30 minutes, then washed and developed with pNPP. A standard curve was obtained against which unknown samples could be determined.

(ii) The plate was coated with BSA-FITC, 10 mg/ml. After blocking and washing, 10 μl and in another series 40 ul of conjugate was added, followed by 100 μl of gentamicin standards. The plate was incubated at 37 C for 1 hr. The plate was washed and antiFab-alklaine phosphatase at 1:1000 dilution was added for 30 minutes at room temperature. The plate was washed and developed with pNPP. A standard curve was obtained against which unknown samples could be determined.

Example 4

Development of an Oestradiol Immunoassay System

Example 1 was repeated changing the digoxin monoclonal antibody for a monoclonal antibody against oestradiol (Biogenesis Ltd, UK, Cat. No. 7010-2190). The digoxin BSA was also replaced by oestradiol-BSA (Sigma Chemical Co Ltd, Cat No. E 5630). A standard curve was obtained against oestradiol enabling unknown samples to be analysed for oestradiol.

Anti-oestradiol IgG1 Fab and anti-FITC IgG1 Fabs were made with the Immunopure kit. The Fab fragments at 0.1 mg/ml were conjugated as above. 1.5 ml of the conjugate was added to 1.5 ml dialysed oestradiol-BSA at 1 mg/ml.

A fluorescein SEPHADEX column was prepared (5 ml) in 0.1 M sodium bicarbonate. The column was washed well with Tris TWEEN buffer. 1.5 ml of the dialysed oestradiol-BSA at 1 mg/ml was run through the column and after washing with Tris TWEEN the Fab conjugate was put on the column, the column run with Tris TWEEN and the eluate collected.

A microtitre plate was coated with anti-mouse IgG1, Fab specific antibody at 10 μg/ml, 100 μl/well in coating buffer. It was left at 37 C for 2 hrs. The plate was blocked with 100 μl/well coating buffer containing 0.2% BSA for 15 minutes at room temperature The anti-FITC-anti-oestradiol Fab conjugate was diluted to a concentration of 10 μg/ml and 10 μl, 50 μl or 100 μl was added to each well in three series of wells. The plate was incubated at room temperature for 1 hr. It was washed in Tris Triton buffer four times. Oestradiol standards were made as: 100 μg/ml in ten fold dilutions to 10 pg/ml. 50 μl of each standard was applied to the plate followed by 25 μl of oestradiol-BSA, 0.4 mg/ml. The plate was incubated at room temperature for 10 minutes. Then 10 μl of a 1:100 dilution of FITC-alkaline phosphatase was added. This was left for 10 minutes at room temperature, washed four times and 200 μl of pNPP was added to each well, incubated, the wells read at 405 nm and the best standard curve for the determination of unknown samples of oestradiol chosen and used to determine unknown samples.

Example 5

Determination of Cortisol

A murine hybridoma cell line which produces a high affinity anti-cortisol monoclonal antibody is obtained, is adapted to alpha MEM medium with 10% heat inactivated calf foetal serum (MEM10%) and is made resistant to thioguanine as follows: 10' hybridoma cells are placed into 2×48 well tissue culture plates in MEM 10% with 20% conditioned macrophage medium from J774 macrophage cells and 5 μg/ml of 6-thioguanine (Sigma Chemical Co Ltd). Resistant clones are obtained after around one month, they are then sub-cultured and the resulting clones checked for maintenance of anti-cortisol antibody production. A healthy fast growing good secretor of anticortisol antibody is chosen (Cort-thio) and used in the following bispecific antibody generation. A Balb/c mouse is immunised over a period of six weeks by standard means with a monoclonal antibody (D-blo-1) the last immunisation being four days before fusion. Splenocytes from this animal are then fused with standard techniques with Cort-thio. Resulting clones producing bispecific antibodies reactive to both cortisol and the immunoglobulin D-blo-1 are then identified as follows. Microtitre strips are coated with D-blo-1 and glazed with BSA. Culture fluid to be tested is added and incubated for one hour at room temperature. The fluid is removed and the plate washed four times with 50 mM Tris buffer pH 7.4 containing 0.02%. Tritiated cortisol is added, incubated for 30 minutes at room temperature, the solution removed and the strip washed again four times after which the individual wells are assessed for their radioactivity. The chosen clones are then grown up and sub-cloned by standard means. They are then reassessed for suitable bispecific antibody production as follows.

In this (Screen B) a microtitre plate is coated with 100 μl anti-mouse IgG and glazed with BSA. 100 μl of culture fluid to be tested is added to the wells and incubated for one hour at room temperature. The solution is replaced with 1 10 μl of a unrelated mouse IgG at 5 μg/ml and incubated for a further 30 minutes. The solution is removed and the wells washed four times. 100 μl of cortisol standards over the range 0, 10 μg/ml and ten-fold increases to 10 μg/ml are added and incubated for ten minutes after which 5 μg of cortisol-keyhole limpet haemocyanin (KLH) conjugated from KLH (Sigma Chemical Co Ltd cat no H 7017) and cortisone 3-(O-carboxymethyl) oxime by standard means is added in 10 μl 50 mM Tris buffer pH 7.6 mixed and incubated for thirty minutes. Following this 10 μl of an alkaline-phosphatase conjugate of D-bio-1 made by standard maleimide hetero-bifunctional linker conjugation is added and mixed and incubated for a further thirty minutes. The solution is removed and the plate washed followed by the standard addition of alkaline phosphatase substrate p-nitrophenol phosphate and development of reaction at 405 nm followed. That clone which gives rise to the best standard curve (Cort-D-blo-1) is adopted as the producer of bispecific antibody and is then further grown up and preserved using standard techniques.

Screen B is repeated with unknown samples the level of cortisol of which may be determined by reference to the standards employed.

Example 6

Example 5 is repeated but employing an anti-idiotypic antibody against the anticortisol antibody in place of the cortisol-KLH blocker.

Example 7

Cort-D-blo-1 is grown up and its bispecific antibody purified. It is the labelled with alkaline phosphatase using standard procedure and used in a diagnostic test for cortisol as follows.

Microtitre plates are coated with 100 μl D-bio-1 and glazed with BSA. Duplicate wells receive (1) 100 μl of a standard cortisol solution of 0.0, 10 pg/ml up in ten-fold concentration steps to 10 μg/ml and unknown standards (2) 5 pg/ml of cortisol-KLH and (3) 10 μl of a 1:1000 dilution of the cort-D-blo-1-alkaline phosphatase conjugate. The wells are incubated for thirty minutes at room temperature, the solutions removed and the wells washed four times. pNPP substrate is then added and the wells monitored at 405 nm. A standard curve of cortisol concentration against optical density is drawn and the concentration of cortisol in the unknowns determined.

Example 8

Example 7 is repeated but instead of cortisol-KLH an anti-idiotypic antibody against the cortisol antibody is used.

Example 9

Determination of Gentamicin with a Specifically Prepared Plate Plate Preparation An anti-IgG Fab antibody is obtained and fragmented by means of the Pierce 34 and Warriner Kit (1995 Cat. No. 44880) to obtain Fab fragments. These are diluted in 50 mM bicarbonate buffer pH 9.6 to 5 μl/ml. 200 μA aliquots are dispensed into the wells of a Nunc microtitre plate and incubated overnight at room temperature after which the solutions are removed and replaced with 0.2% bovine serum albumin (BSA) in the same buffer. The plate is left at room temperature for 30 minutes after which it is washed four times with wash solution of 50 mM Tris pH 7.4 containing 0.02% TWEEN 20.

An IgG monoclonal antibody is obtained against gentamicin. It is fragmented by means of the Pierce and Warriner Kit (1995 Cat No. 44880) to yield Fab fragments. These are conjugated to bovine serum albumin, being mixed at a molar ratio of 1 (Fab):10 (BSA) after which the mixture is treated with the hetero-bifunctional reagent ethylene glycol bis(succinimidyl succinate) (EGS) (Abdelia et al Biochem. & Biophys. Res. Corns. (1979) 87; 734. (Pierce & Warriner 1995 Cat. No. 21565). Dimer conjugates are then isolated means of size exclusion chromatography to provide reagent 'Fab-conj' without attempt at removal of BSA homo-dimer conjugates. The dimer conjugate solution is diluted to 15 μg/ml in 50 mM Tris pH 7.4 and 180 μl applied to each well of the microtitre plate and incubated for one hour at room temperature. The solution is removed and the plate washed four times with wash solution. 200 μl of a solution of 0.05M lysine containing 1M hydroxylamine at pH 8.5 is added and the plate incubated for four hours at 37 C with changes of the hydroxylamine solution after two and thirty minutes. The plate is again washed four times and 175 μl of a solution of an Fab fragment of an anti-fluorescein IgG monoclonal antibody (prepared as with the gentamicin Fab fragment by employing the Pierce and Warriner Kit) at a concentration of 1 µg/mL in 50 mM Tris buffer pH 7.4. The plate is incubated for one hour at room temperature the solutions removed and the plate washed four times in wash solution. It is now ready for use.

Gentamicin Assay:

Into the wells of the prepared plate are placed: 175 µA of a series of gentamicin standards (from 10 pg/ml to 10 µg/ml in ten fold steps and zero standards) and samples with unknown concentrations of gentamicin. The plate is incubated for ten minutes at room temperature. 15 µl of a 200 µg/ml solution of gentamicin-BSA (Biogenesis 199596 Cat. No. 4630-0604) is then mixed into each well and the plate incubated for a further ten minutes. This is followed by a further ten minute incubation after the addition to each well of 10 µl of a solution of a fluorescein-alkaline phosphatase conjugate prepared by standard means from fluorescein isothiocyanate (Sigma Chemical Co. Ltd 1994 Cat, No. F 4274) and bovine intestinal alkaline phosphatase (Sigma Chemical Co Ltd 1994 Cat. No. P 5221) followed by purification by means of a SEPHADEX G-150 chromatography column. The solution is removed and the wells washed four times. 200 µl of a 50 mM solution of bicarbonate buffer pH 9.3 containing 3.3 mM $MgCl_2$ is then added to each well and the wells monitored at 405 nm. Readings from all wells are taken when the fastest developing well reaches an optical density of 1.8 and a graph is plotted of optical density against gentamicin concentration from which the concentration of gentamicin in unknowns is calculated.

Example 10

Preparation of Dual Specific Antibody Reagent

An immunogenic conjugate of vasopressin (Calbiochem-Novabiochem UK Ltd. product number 05-23-0155) is made employing activated carrier bovine serum albumin from Pierce & Warriner U.K. (cat. Imject Maleimide Activated BSA product number 77115). Polyclonal antibody is raised against this and purified by conventional means employing ammonium sulphate fractionation and DEAE chromatography.

Following the basic protocol of Pierce & Warriner (0589) Sulfo-SBED (2-[6-(Biotinamido)-2-(p-azidobenzamido)-hexanamido]ethyl-1-3'-dithio-propionate) (Pierce & Warriner product number 33033) may then be used to obtain a preparation of the antibody conveniently biotinylated around the binding site as follows.

Continuously in the dark until the photoactivation step, 5 mg of vasopressin hapten is dissolved in 0.5 ml of 0.1M phosphate buffered saline at pH 7.2 in a microcentrifuge tube. 1.12 mg of Sulfo-SBED is then dissolved in 25 µl DMSO and 11 µl are added to the vasopressin solution. This is then incubated at room temperature for 30 minutes. The solution is then centrifuged for 1 min and the solution carefully removed and separated free from unreacted Sulfo-SBED.

The biotinylated hapten is then mixed with 5 mg of antibody dissolved in 0.5 ml PBS and incubated in the dark at room temperature for 10 minutes. Scavenger p-aminobenzoic acid is then added and it is the photolysed with a long wave UV lamp (365 nm) at a distance of 5 cm for 15 minutes. The mixture is then desalted using a 10 ml desalting column equilibrated with PBS 1 ml fractions being collected the protein fractions being pooled. The disulphide bond of the spacer arm is the disrupted by incubation with 50 mM dithiothreitol (DTT). This preparation is termed (DBab1). The excess DTT as well as unconjugated antibody is then be removed by means of an anti-biotin column. The mixture is applied to a biotin agarose column (Sigma Chemical Co Ltd product number A 1559), the eluant discarded and the purified antibody eluted with elution buffer and dialysed against PBS. This antibody is termed double-binder antibody (DBab1).

The DBab may be further purified before use to remove antibody which has received unwanted biotin residues at positions in which the binding of the residues is not inhibited by binding of the binding site by hapten analogue as follows.

The 0.5 mg of DBab is incubated with 5 mg of vasopressin-BSA in 2 ml PBS. This is then reapplied to an anti-biotin antibody column as previously used but this time the protein which passes straight through the column is collected and used. It is applied to a Protein A column and unbound vasopressin BSA washed and eluted away. The antibody is then eluted after which 5 mg of free vasopressin is added, the mixture incubated in the presence of azide for 24 hrs and the reapplied to a fresh protein A column. Again the first eluant and washings are discarded and the bound antibody subsequently removed from the column. It is the subjected to extensive dialysis to remove remaining vasopressin before use.

Vasopressin Assay

The wells of Nunc microtitre plates are coated with 100 µl solutions of 2 µg/ml of DBab in coating buffer by being left overnight at 4° C. They are then glazed by the addition of 200 µl of 0.2% BSA in coating buffer which is left in the wells for 30 minutes at room temperature. The solution is then removed and the wells washed four times in washing buffer. Standard solutions of vasopressin are made from 10 µg/ml to 1 pg/ml in ten fold dilutions of buffer. 100 µl of each are added to individual wells and other wells receive 100 µl of test samples containing unknown amounts of vasopressin. Each well then receives 20 µl of a 20 µg/ml solution of the vasopressin-BSA conjugate previously made and employed for immunisation is added with mixing. The plate is left for 20 minutes at room temperature after which 10 µl of an anti-biotin antibody alkaline phosphatase conjugate (Sigma Chemical Co Ltd cat number A 7064) diluted at 1:20,000 is mixed into each well and the wells left for a further 20 minutes at room temperature. The solutions are removed from the wells and the wells washed four times. 100 µl of a standard assay substrate solution of para-nitrophenol phosphate (Sigma Chemical Co Ltd cat number N 2770) is added to each well and the plate monitored at room temperature in a microtitre plate reader at 405 nm. The whole plate is read when the fastest developing well reaches an optical density of around 2.0. A standard curve is drawn of vasopressin standard concentration against optical density and the concentration of vasopressin in the unknown test samples determined with this from the optical density they achieved during the assay.

Example 11

The DBab1 of example 10 may be alternatively derived as follows. The antibody (calculated as 30 mg) is applied to a Protein A column (Pierce & Warriner product 44898) which is then washed. The Sulfo-SBED linked vasopressin made up to 2 ml in PBS is then run slowly into the column, the flow stopped the column left for thirty minutes at room temperature and then washed with 20 ml of PBS. The column material is then removed from the column suspended in 10 ml PBS containing scavenger p-aminobenzoic acid and while gently mixing illuminated with a long wave UV lamp (365 nm) at a distance of 5 cm for forty minutes. The material is packed back to reform the column which is then washed with 10 ml of PBS. The linked antibody is then removed from the column with the proprietary solution supplied by Pierce & Warriner. It is then placed in a dialysis sack and dialysed in PBS containing 50 mM DTT (Sigma Chemical Co Ltd). The antibody is then made 3M in ammonium thiocyanate and applied to a desalting column (Pierce and Warriner product number 20290) previously equilibrated with 3M ammonium thiosulphate in PBS. The first protein antibody fractions are pooled and then dialysed against PBS containing 0.05% sodium azide preservative. This antibody is termed double-binder antibody (DBab1) and used as in the previous example.

Example 12

Example 10 Vasopressin assay is repeated for Substance P replacing Substance P for vasopressin throughout the example and an anti-Substance P monoclonal antibody in place of the anti-vasopressin polyclonal antibody and a protein G column replacing the protein A column.

Example 13

Vasopressin Assay

The wells of Nunc microtitre plates are coated with 100 µl solutions of 2 µg/ml of anti-gamma chain antibody (Sigma Chemical Co Ltd Cat number R 1008) in coating buffer by being left overnight at 4° C. They are then glazed by the addition of 200 µl of 0.2% BSA in coating buffer which is left in the wells for 30 minutes at room temperature. The solution is then removed and the wells washed four times in washing buffer. 104l of the purified DBab preparation are then added to each well and the plate incubated for one hour at room temperature. The solutions are removed and the wells washed four times with washing solution. Standard solutions of vasopressin are made from 10 µg/ml to 1 µg/ml in ten fold dilutions of buffer. 100 µl of each are added to individual wells and other wells receive 100 µl of test samples containing unknown amounts of vasopressin. Each well then receives 20 µl of a 10 µg/ml solution of the vasopressin-BSA conjugate previously made and employed for immunisation is added with mixing. The plate is left for 20 minutes at room temperature after which 1 µl of an anti-biotin antibody alkaline phosphatase conjugate (Sigma Chemical Co Ltd cat number A 7064) diluted at 1:20,000 is mixed into each well and the wells left for a further 20 minutes at room temperature. The solutions are removed from the wells and the wells washed four times. 100 µl of a standard assay substrate solution of p-nitrophenol phosphate (Sigma Chemical Co Ltd cat number N 2770) is added to each well and the plate monitored at room temperature in a microtitre plate reader at 405 nm. The whole plate is read when the fastest developing well reaches an optical density of around 2.0. A standard curve is drawn of vasopressin standard concentration against optical density and the concentration of vasopressin in the unknown test samples determined with this from the optical density they achieved during the assay.

Example 14

Determination of Substance P

Example 13 is repeated for Substance P replacing Substance P for vasopressin throughout the example and an anti-Substance P monoclonal antibody in place of the anti-vasopressin polyclonal antibody and a protein G column replacing the protein A column to give rise to an system for the measurement of Substance P.

Example 15

Preparation of Apposition Reagent

A murine anti-folic acid monoclonal antibody was biotinylated close to the antigen binding site by the following protocol.

8 mg NHS (N-Hydroxysuccinimide) was added to 16 mg folic acid in 4 ml DMSO solvent followed by 9 mg of DCC (dicyclohexyl carbodiimide) in 500 µl DMSO. It was then incubated at room temperature for 2 h then added to 4.7 mg Diaminohexane in 500 µl DMSO forming a white-yellow precipitate/suspension. It was left overnight to react to completion forming the folate-diaminohexane linker. 156 µl of this was then added to 1 mg of Sulfo-SBED (2-[(6-(Biotinamido)-2-(p-azidobenzamido)-hexanamido]ethyl-1-3'-dithio-propionate) (Pierce & Warriner product number 33033) in 100 µl DMF and incubated for a further 48 h during which time the solution clarified. This was followed by the addition of 750 µl distilled water to neutralise any tridentate-NHS ester groups which might have remained. After a further 4 h 500 µl of this hydrolysed tridentate-folate complex was added to 1 mg (500 µl) of antibody and incubated for a further 48 h.

Excess Tridentate-folate was removed by passage through a small P10 desalting column in 50 mM Phosphate buffer pH7.5 in the dark. 1 ml fractions were taken. The majority of eluted antibody (0.8 mg) came off of the column in tube 4. The contents of this tube were UV-irradiated for 10 min in a quartz cuvette. 7 µl mercaptoethanol was then added and incubated for 15 minutes at room temperature to reduce the disulphide bond of the tridentate. It was then dialysed against 50 mM phosphate buffer pH7.5 initially containing 1M NaCl for 24 h and then with no added NaCl for a further 24 h to remove mercaptoethanol and any remaining folate residue. 1 ml 1M Acetic Acid was then added to the dialysis bag to completely dissociate folate residue followed by immediate dialysis against 2 L of 50 mM phosphate pH7.5 for 2 days. The antibody was then ready for use.

Use of Apposition Reagent

The apposition reagent was coated onto a plate in 100 µl aliquots at 3 µg/ml in coating buffer of 50 mM carbonate/bicarbonate pH9.6 overnight, 4° C. Wells were then glazed with 100 µl blocking solution of coating buffer containing 0.5% Bovine Serum Albumin, 1 hour, room temperature. The solutions were discarded from the wells and the plate was washed with wash buffer (Wash buffer −50 mM Tris buffer pH 7.4 containing 0.005% Triton) by means of a plate washer.

In the well of a mixing plate were mixed: 60 µl Folate standards from 10 µg/ml, in 3-fold dilutions to 0.014 µg/ml in TBT+buffer (50 mM Tris buffer pH 7.4 containing 0.005% Triton +0.2% Bovine Serum); 60 µl Folate-BSA at 32 µg/ml in TBT buffer (50 mM Tris buffer pH 7.4 containing 0.005% Triton). 100 µl of the mixtures were then transferred to the washed tridentate plate and incubated for 1 hour at room temperature. The plate was then washed with washing buffer. 100 µl Mab anti-Biotin-AP (Sigma Chemical Co Ltd [BN34] cat A6561) at 1:2000 dilution was added and incubated for 1 hour at room temperature. The plate was again washed with wash buffer followed by the addition of 100 µl of pNPP (para-nitrophenyl phosphate) substrate in substrate buffer of 50 mM carbonate/bicarbonate pH10.3+3.3 mM $MgCl_2$. The plate was then monitored at 405 nm. A set of readings was taken when it was judged that sufficient development had taken place.

The resulting data was as follows, from which a standard curve was drawn to determine unknown samples assayed by the method.

| Folate (µg/ml) | OD 405 nm | | | Mean OD |
|---|---|---|---|---|
| 0.01 | 0.421 | 0.417 | 0.441 | 0.426 |
| 0.03 | 0.483 | 0.482 | 0.401 | 0.455 |
| 0.1 | 0.536 | 0.483 | 0.502 | 0.507 |
| 0.3 | 0.667 | 0.628 | 0.623 | 0.639 |
| 1 | 0.917 | 0.872 | 0.855 | 0.881 |
| 3 | 1.254 | 1.263 | 1.205 | 1.241 |
| 10 | 1.696 | 1.632 | 1.589 | 1.639 |

Example 16

Elisa System for Benzoylecgonine (BE)

Example 14 was repeated for Benzoylecgonine (BE) employing a specific BE-KLH blocker and anti-BE antibody specifically derivitised with a tridentate-BE conjugate.
Preparation of Apposition Reagent
A specific monoclonal antibody was obtained against Benzoylecgonine (BE). BE was treated with carbodiimide and a 6 carbon diamine linker in dry solvent to convert the BE-COOH group to an amine group via the 6 carbon chain. This drug-diahexamine derivative was then added at a 1:1 molar ratio to the trifunctional (tridentate) SBED reagent ((2-[6-(Biotinamido)-2-(p-azidobenzamido)-hexanamido]ethyl-1-3'-dithiopropionate) (Pierce & Warriner product number 33033), again in dry solvent, to allow the amine groups on the BE derivative to react with the sulpho-NHS arm of the tridentate. The mixture was incubated for 36-48 h in the dark after which a 30-fold excess (330 ug) of drug-SEED reagent was added to 1 mg of the antibody (in 1 ml aqueous buffer). This was again left for 36 hours to facilitate binding. Unbound SBED-BE conjugate was then removed from the antibody by passage through a G25 column. The purified antibodies were then immediately irradiated with UV light as in the previous example. Mercaptoethanol was then added to split the tridentate SBED-BE complex into two halves. Free BE was then removed from its binding site by treatment with 1M acetic acid followed by repeated dialysis in 10 mM phosphate buffer pH7.4. The biotin derivatised anti-BE agent (BE-Bio) was then ready for use.
Preparation of Blocker
BE was conjugated through a 6 carbon diaminohexane linker to KLH. The conjugate was then extensively dialysed. The ability of the blocker to bind to the anti-BE antibody was then checked by coating it onto a microtitre plate which was then glazed and washed. Purified anti-BE antibody was shown to bind the blocker, itself being detected by means of an alkaline phosphatase labelled anti-IgG antibody. Binding of anti-BE antibody was shown to be inhibited by addition of free BE to the anti-BE antibody added to the plate.
Use of Apposition reagent
The wells of a microtitre plate were each coated with 100 µl of a solution of 10 µl/10 ml Fc-specific anti-murine IgG in TT buffer and then glazed as in the previous example. 100 µl of derivitised anti-BE antibody at a concentration of 30 µg/10 ml Tris TWEEN buffer was added to the test wells (with wells to determine plate background receiving only buffer) and left at room temperature for one hour. The solutions were removed and the plate washed to provide an 'ap.test plate'. A BE-KLH concentration series was run to establish the concentration of BE-KLH blocker required to adequately inhibit the binding of alkaline phosphatase conjugated anti-biotin to the biotinylated anti-BE antibody.

To the individual wells of an 'ap.test plate' were added 50 µl of BE standards (a standard dilution series of BE from 2.0 µg/ml in three-fold dilutions to 2.7 ng/ml plus a zero standard solution) followed by addition, with mixing, of 50 µl of the BE-KLH blocker at 20 µl/ml to each well. The plate was incubated at room temperature for 45 minutes after which a further 50 µl of technical grade mouse IgG was added and the plate incubated for a further 15 minutes. The solutions were shaken out and the plate again washed. 100 µl of a solution of 10 µl technical grade IgG and 3.5 µl alkaline phosphatase conjugated anti-biotin antibody (Sigma Chemical Company Ltd) in 10 ml TT buffer was added to each well and incubated for 1 hr at room temperature. The solutions were discarded and the plate washed. 100 µl of a 20 mg/10 ml p-nitrophenyl phosphate substrate in 50 mM bicarbonate buffer pH 10.3 was then added to each well and the rate of colour development at 405 nm monitored with a plate reader. The results were as follows after a twenty minute incubation:

| BE (µg/ml) | OD 405 nm | | Mean OD |
|---|---|---|---|
| Background | 0.113 | 0.102 | 0.108 |
| 0.008 | 0.524 | 0.517 | 0.521 |
| 0.025 | 0.517 | 0.528 | 0.523 |
| 0.074 | 0.603 | 0.683 | 0.643 |
| 0.222 | 0.825 | 0.744 | 0.785 |
| 0.667 | 0.948 | 0.858 | 0.903 |
| 2.00 | 1.051 | 1.040 | 1.045 |

From this data, a standard curve is drawn to detect BE concentration in unknown samples analysed by the method.

Example 17

Vitamin B12 System

Example 14 was repeated with vitamin B12 instead of folate. A monoclonal antibody against vitamin B12 was derivatised with a tridentate-B12 conjugate. This was then successfully used in a system analogous to that for folate for the determination of vitamin B12.

Example 18

Lateral-Flow Dip Stick for Benzoylecgonine (BE)

5 mm wide 8 micron nitrocellulose dip sticks with polyester support and sample delivery pads were normally stripped with a fine line of a solution of 0.5 mg/ml anti-biotin antibody to provide a detector line. Biotin derivatised anti-BE agent prepared in Example 15 (BE-Bio) was bound by adsorption at 2.5 µg/ml to 40 nm gold particles at an optical density of 1 at 530 nm. The particles were washed and concentrated to give a working suspension at 530 nm of 10.
Into the mixing wells of a microtitre plate were added: 30 µl of the gold suspension, 70 ul Tris/Triton pH 7.4, 10 µl of 0.2 mg/ml BE-KLH blocker (as in the previous example) and 100 µl sample/standard solutions prepared from a stock solution of 10 µg/ml BE employing 0, 2, 5 and 10 µl per 100 µl. They were left for 15 minutes at room temperature. The sample addition pads of the dip sticks were placed into individual mixing wells and the contents allowed to migrate up the sticks. The sticks were placed in a further 100 µl of buffer. Those sticks placed in wells containing BE showed clearly more marked bands of red gold at their detector lines than the zero standard. This may be used to show the presence of BE in a sample.

Example 19

Indirect Lateral-Flow Dip Stick for Benzoylecgonine (BE)

Example 17 was repeated but instead of employing gold particles directly coated with the Biotin derivatised anti-BE agent, gold particles coated with anti-murine-Fab antibody were used. These were mixed with the BE-Bio at a suitable concentration to provide good binding but not over-saturation (optionally these can be washed free of unbound Biotin derivatised agent). These particles were used in place of the directly coated gold particles again providing an dip stick assay system for the samples/standards given above which showed clear development of a red detector line for BE positive standards over the zero sample.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. The references in the above text and listed below are incorporated by reference insofar as is required for the skilled person to carry out the invention.

The invention claimed is:

1. A method of determining an analyte of molecular weight less than 1,500 Daltons in a sample, which method comprises contacting the sample with:
   (i) an analyte analogue;
   (ii) a modified binding agent; and
   (iii) a reporter molecule;
   and
   determining the amount of reporter molecule interacting with the modified binding agent;
   wherein the modified binding agent is a binding agent having an analyte binding site capable of binding said analyte of molecular weight less than 15000 Daltons and capable of binding said analyte analogue, said modification comprising creating a reporter site adapted to interact in a detectable manner with the reporter molecule when the modified binding agent binds said analyte but not when the modified binding agent binds said analyte analogue.

2. A method according to claim 1 wherein said reporter molecule binds to said reporter site.

3. A method according to claim 1 or claim 2 wherein said reporter site is created by chemical modification of the binding agent.

4. A method according to claim 3 wherein said reporter site is created by coupling biotin to said binding agent.

5. A method according to claim 1 or claim 2, wherein said reporter site is created by modification of nucleic acid encoding the binding agent.

6. A method according to claim 5 comprising addition, substitution or deletion of at least one amino acid of the binding agent.

7. A method according to clam 5 or claim 6 wherein said reporter site is a known epitope for an antibody.

8. A method according to claim 1 wherein said analyte analogue prevents binding between said reporter molecule and said binding agent by steric hindrance or electrostatic repulsion.

9. A method according to claim 1 wherein said binding agent is an antibody or an enzyme.

10. A method according to claim 1 wherein said analyte analogue is an antibody directed against said analyte binding site.

11. A method according to claim 1 wherein the analyte is a drug of abuse or a metabolite thereof, such as cocaine or benzoyl ecgonine.

* * * * *